(12) United States Patent
Gruber et al.

(10) Patent No.: US 10,564,091 B2
(45) Date of Patent: Feb. 18, 2020

(54) OPTICAL SENSING DEVICE WITH MULTIPLE FIELD-ENHANCED NANO-VOLUMES

(71) Applicants: International Business Machines Corporation, Armonk, NY (US); ETH Zurich, Zurich (CH)

(72) Inventors: Cynthia Gruber, Rueschlikon (CH); Lars Herrmann, Rueschlikon (CH); Emanuel Marc Lörtscher, Bonstetten (CH); Bruno Michel, Zurich (CH); Lukas Novotny, Zurich (CH)

(73) Assignee: International Business Machines Corporation, Armonk, NY (US)

( * ) Notice: Subject to any disclaimer, the term of this patent is extended or adjusted under 35 U.S.C. 154(b) by 353 days.

(21) Appl. No.: 15/681,371

(22) Filed: Aug. 19, 2017

(65) Prior Publication Data

US 2019/0056309 A1 Feb. 21, 2019

(51) Int. Cl.
*G01N 33/551* (2006.01)
*G01N 21/01* (2006.01)
(Continued)

(52) U.S. Cl.
CPC ......... *G01N 21/01* (2013.01); *G01N 21/6486* (2013.01); *G01N 21/658* (2013.01); *G01N 33/54373* (2013.01)

(58) Field of Classification Search
None
See application file for complete search history.

(56) References Cited

U.S. PATENT DOCUMENTS 7,949,210 B2 5/2011 Durfee et al.
8,158,409 B2 4/2012 Wei et al.
(Continued)

FOREIGN PATENT DOCUMENTS

EP 2878373 A1 6/2015
WO 2012078099 A1 6/2012
(Continued)

OTHER PUBLICATIONS

Fleischer, M., et al. "Self-aligned Fabrication of Hybrid Nano-antenna/Nano-particle Systems for Optical Sensing and Spectroscopy." Session 2P7a SC3: Advanced Micro-/Nano-fabrication for Optical Sensing and Imaging Applications: Aug. 2014 p. 825(Abstract Only).

(Continued)

*Primary Examiner* — Christopher L Chin
(74) *Attorney, Agent, or Firm* — Daniel P. Morris; Otterstedt, Wallace & Kammer, LLP

(57) ABSTRACT

An optical sensing device includes a substrate; a first dielectric layer extending thereon; a plurality of pairs of opposite antennas patterned on the first layer; and a second dielectric layer that covers all of the antennas. Opposite antennas are, in each of the pairs, separated by a gap g, which, on average, is between 1 nm and 50 nm, as measured in a direction x parallel to a main plane of the substrate. The pairs of antennas have different geometries. The second layer covers all the antennas and defines an electro-magnetic field enhancement volume between the opposite antennas of each of the pairs, thanks to the gap. Electro-magnetic radiation can be concentrated in each volume, making it possible to optically sense an analyte via opposite antennas of each of the pairs. Such a device allows analytes to be funneled and guided into the field-enhanced volumes for deterministic sensing.

20 Claims, 7 Drawing Sheets

(51) Int. Cl.
*G01N 21/65* (2006.01)
*G01N 33/543* (2006.01)
*G01N 21/64* (2006.01)

(56) References Cited

U.S. PATENT DOCUMENTS

| | | |
|---|---|---|
| 8,462,334 B2 | 6/2013 | Lu et al. |
| 8,537,353 B2 | 9/2013 | Liu et al. |
| 9,157,861 B2 | 10/2015 | Bai et al. |
| 9,255,843 B2 | 2/2016 | Yu et al. |
| 9,274,053 B2 | 3/2016 | Escobedo et al. |
| 9,309,590 B2 | 4/2016 | Baldauf et al. |
| 9,453,814 B2 | 9/2016 | Tran |
| 2007/0058686 A1* | 3/2007 | Capasso ............ B82Y 20/00 372/43.01 |
| 2009/0052827 A1 | 2/2009 | Durfee et al. |
| 2010/0284012 A1 | 11/2010 | Chinowsky et al. |
| 2013/0065777 A1 | 3/2013 | Altug et al. |
| 2014/0045730 A1 | 2/2014 | Walters |
| 2014/0313507 A1 | 10/2014 | Fernandez-Cuesta et al. |
| 2014/0339090 A1 | 11/2014 | Huang et al. |

FOREIGN PATENT DOCUMENTS

| | | |
|---|---|---|
| WO | 2015026297 A1 | 2/2015 |
| WO | 2015081294 A2 | 6/2015 |

OTHER PUBLICATIONS

Kimani C. Toussaint Jr., et al., Plasmonic Nanoantennas: From Nanotweezers to Plasmonic Photography, Optics & Photonics News Jun. 2015, cover plus pp. 26-31.

Ahmadian, D., Ch Ghobadi, and J. Nourinia. "Ultra-compact two-dimensional plasmonic nano-ring antenna array for sensing applications." Optical and Quantum Electronics 46.9 (2014): 1097-1106 (Abstract Only pp. 1-3).

Jaeyoun Kim, Joining plasmonics with microfluidics: from convenience to inevitability, Lab Chip, 2012, 12, 3611-3623.

Xudong Fan and Ian M. White, Optofluidic Microsystems for Chemical and Biological Analysis, Nat Photonics. Oct. 1, 2011; 5(10): 591-597. doi:10.1038/nphoton.2011.206.

Eftekhari, Fatemeh, et al. "Nanoholes as nanochannels: flow-through plasmonic sensing." Analytical chemistry 81.11 (2009): 4308-4311 (Abstract Only pp. 1-2).

Ahmet Ali Yanik, et al., Integrated nanoplasmonic-nanofluidic biosensors with targeted delivery of analytes, Applied Physics Letters 96, 021101-1 through 3 plus cover 2010.

Escobedo, Carlos, et al. "Optofluidic concentration: plasmonic nanostructure as concentrator and sensor" Nano letters 12.3 (2012): 1592-1596. Abstract only pp. 1-2.

Aksu, Serap, et al. "High-throughput nanofabrication of infrared plasmonic nanoantenna arrays for vibrational nanospectroscopy." Nano letters 10.7 (2010): 2511-2518. Abstract only pp. 1-2.

Mazzotta, Francesco, Fredrik Höök, and Magnus P. Jonsson. "High throughput fabrication of plasmonic nanostructures in nanofluidic pores for biosensing applications." Nanotechnology 23.41 (2012): 415304. Abstract only pp. 1-3.

Mazzotta, Francesco, Fredrik Höök, and Magnus P. Jonsson. "High throughput fabrication of plasmonic nanostructures in nanofluidic pores for biosensing applications." Nanotechnology 23.41 (2012): 415304. Full Paper pp. 1-8.

Ahmadian, D., Ch Ghobadi, and J. Nourinia. "Ultra-compact two-dimensional plasmonic nano-ring antenna array for sensing applications." Optical and Quantum Electronics 46.9 (2014): 1097-1106 Full Paper.

Eftekhari, Fatemeh, et al. "Nanoholes as nanochannels: flow-through plasmonic sensing." Analytical chemistry 81.11 (2009): 4308-4311 Full Paper.

Escobedo, Carlos, et al. "Optofluidic concentration: plasmonic nanostructure as concentrator and sensor." Nano letters 12.3 (2012): 1592-1596. Full Paper.

Aksu, Serap, et al. "High-throughput nanofabrication of infrared plasmonic nanoantenna arrays for vibrational nanospectroscopy." Nano letters 10.7 (2010): 2511-2518. Full Paper.

* cited by examiner

OPTICAL SENSING DEVICE WITH MULTIPLE FIELD-ENHANCED NANO-VOLUMES

BACKGROUND

The invention relates in general to the field of nanoscale optical sensing devices and, in particular, to optical devices allowing Raman spectroscopy, conducted on very small quantities of analytes in field-enhanced volumes, through optical antennas.

Direct optical sensing of molecular compounds requires chemical bond-specific signatures to unambiguously detect and identify the analytes under test. Commonly employed gas/liquid chromatography combined with mass spectroscopy allows molecular compounds to be identified due to their distinct mass-charge ratio. However, such a method does not make it possible to retrieve chemical information, namely the chemical bonding properties of the atoms, from the sample. Electrical vibration spectroscopy (e.g., Inelastic Electron Tunneling Spectroscopy) directly reveals the chemical binding energies of a molecular compound but with low energy resolution (e.g., 5 meV/~40 cm$^{-1}$) and, this, only in a very narrow energy range (up to a few 100 mV/~800 cm$^{-1}$).

Besides chromatography-mass spectrometry, fluorescence measurements typically require the attachment of fluorescent labels to the analyte, because the inherent fluorescence of the analytes is usually too weak or not present at specific wavelengths. Such a labelling technique is invasive, can interfere with parameters inherent to the molecules under study and is sometimes not applicable if the native analytes have to be detected without previous labeling.

Optical methods based on elastic or inelastic light scattering at molecular bonds such as absorption or Raman spectroscopy provide sufficient resolution (<0.1 meV/<1 cm$^{-1}$) to unambiguously identify and differentiate chemical bonds over an extended energy range (~500 meV/~4 000 cm$^{-1}$), thereby enabling a comprehensive analysis. While Raman spectroscopy is non-invasive, its major drawback, however, is that it suffers from a very low optical scattering cross-section, i.e., on the order of $10^{-30}$ to $10^{-31}$ cm$^2$/sr, that is, about 1 000 times smaller than the cross section for elastic Rayleigh light scattering or absorption. To overcome the low interaction mechanism, millions of identical molecules need typically be probed simultaneously, in multi-path geometries or during long integration times to obtain detectable signal levels. This limitation has, so far, prevented the use of Raman spectroscopy for detection of small volumes, low analyte concentrations and on fast time scales.

SUMMARY

According to a first aspect, the present invention is embodied as an optical sensing device. This device comprises: a substrate; a first dielectric layer extending on the substrate; a plurality of pairs of opposite antennas (or antenna elements); and a second dielectric layer that covers all of the antennas. The plurality of pairs of opposite antennas are patterned on the first dielectric layer. Opposite antennas are, in each of the pairs, separated by a gap g, which, on average, is between 1 nm and 50 nm, as measured in a direction x parallel to a main plane of the substrate. The pairs of antennas have different geometries. The second dielectric layer covers all of the antennas, so as to define an electro-magnetic field enhancement volume between the opposite antennas of each of the pairs, thanks to the gap g in between. Each volume is such that electro-magnetic radiation can be concentrated therein, which makes it possible to optically sense an analyte via opposite antennas of each of the pairs, in operation.

Present Inventors have developed inverse fabrication methods that make it possible to achieve well-defined, nanometer-ranged gaps between antennas. Owing to their dimensions, the field-enhancement volumes formed between opposite antennas allow unprecedented concentration of electro-magnetic radiation, at the nanoscale. In addition, preferred fabrication methods make it possible for analytes to be deterministically funneled into the field-enhanced regions, where they can be detected through surface enhanced spectroscopies (e.g., surface-enhanced Raman, infrared absorption or fluorescence) as well as intensity and phase changes based on resonance shifts.

The present approach opens up a broad range of new measurement techniques as well as sensing modalities, which can be applied to very small quantities of analytes, e.g., down to a single molecule. Amongst other advantages, this approach enables high integration densities and hyperspectral sensing abilities with multi-resonance antennas, chiral field generation and loss suppression through exploitation of polarization. Additionally, the field enhancements and field gradients obtained thanks to the very small gaps make it possible for optical selection rules to be altered, hence creating access to infrared modes through Raman spectroscopy under so-called field-gradient Raman conditions. Moreover, optically non-interfering electrical gating capabilities, as enabled by the present devices, allow for additional sensing modalities, analyte release functionality (in case of active binding) and thermal control of nanochemical reactions, including cooling or heating.

In embodiments, the gaps separating the antennas of each of the pairs are essentially constant, subject to ±0.1 nm, owing to preferred fabrication methods as used to obtain such devices.

In preferred embodiments, electro-magnetic field enhancement volumes defined between the antennas of each of the pairs are, each, between 1 nm$^3$ and 10$^5$ nm$^3$, which allow extreme field intensity and field gradient conditions to be achieved.

Optionally, the pairs of antennas may have different lengths, so as to be able to tune the optical resonances. Said lengths are measured between outermost ends of opposite antennas of each of the pairs along that same direction x.

Optionally, opposite antennas within each of one or more of the pairs may have different lengths, as measured along said direction x, or distinct geometries. This way, asymmetric antennas are obtained, which allow tailored optical resonances and optical non-linearities to be achieved. For example, this makes it possible to tune the resonance over a wider spectral range, giving access to high-order or non-linear modes. Furthermore, asymmetric antennas can be tailored to harness specific polarization states of the incident light.

In embodiments, antennas of one of more of the pairs have a form factor, such that their largest dimension is parallel to said direction x. This makes it easier to achieve resonance shifts (as in typical applications), which lead to measurable changes in the scattered/transmitted intensities of the antennas once an analyte is present in the gap.

Preferably, the present optical sensing device further comprises chemical receptor layers oppositely arranged on opposite, inner faces of opposite antennas of one or more of the plurality of pairs. This makes it possible for the antennas' inner facets to (reversibly) bind specific types of analytes only (in order to increase their relative concentration or residence time in the field enhancement volume without making the sensor a single use device), as required in applications, e.g., relying on resonance shifts as indirect sensing modality rather than direct optical sensing by spectroscopy.

In preferred embodiments, the device comprises a channel, along which opposite antennas of each of the pairs are arranged, in vis-à-vis. The channel is configured so as to enable fluid communication between the plurality of field enhancement volumes defined between opposite antennas of each pair. I.e., this channel is configured so as to enable analyte delivery in liquid (fluid) or gas phase, and funneling along the antenna pairs, as well as interaction between the electro-magnetic field and analyte in the field enhancement volumes, to take advantage of sensing modalities enabled by the distinct pairs of antennas.

Preferably, opposite antennas of each of the pairs are patterned along a section of the channel that extends parallel to a direction y, which is parallel to the main plane of the substrate and perpendicular to said direction x. In addition, a minimal separation between contiguous pairs of antennas, as measured along said direction y, is of at least 1 nm. A larger separation may for instance be desired to avoid inter-pair crosstalk effects, e.g., when performing amplified Raman signal detection. Yet, a small separation may be desired to create hybrid induced charge distributions among multiple pairs of antennas.

In embodiments, one or each of the antennas of one or more of the pairs is at least partly embedded, laterally, in a dielectric structure, the latter shaped so as to define lateral walls of the channel. Said walls extend perpendicular to the main plane of the substrate. Embedding antennas in dielectric structures allows improved control over the analyte funneled into the channel and, this, possibly in a deterministic way. The dielectric structures further protect the antenna (e.g., to prevent oxidation), as they prevent direct contact with (at least a part of) the antenna.

Preferably, the substrate comprises a recess, over which the first dielectric layer extends, such that a recessed portion of the first dielectric layer is arranged on the recess, whereas a peripheral portion of the first dielectric layer extends over a peripheral region of the substrate, around the recess. The recessed portion is recessed from said peripheral portion of the first dielectric layer, in a direction z perpendicular to the main plane of the substrate. In addition, said one or each of the antenna is patterned on the recessed portion of the first dielectric layer and the peripheral portion is further patterned so as to form the dielectric structure, in which said one or each of the antennas is at least partly embedded, laterally. Providing such a recess, with antennas patterned thereon, is notably useful when relying on a chemical mechanical polishing process to refine, reduce, planarize and smoothen transverse features of the device. That is, the recess layer enables accurate stopping of the chemical mechanical polishing process. In preferred embodiments, said one or each of the antennas is only partly embedded, laterally, in said dielectric structure, whereby a void is defined between said one or each of the antennas and a portion of said dielectric structure. This makes it possible for the antennas to be partly isolated from the surrounding, embedding structures. Preferably, said void is defined at an outermost end of said one or each antenna, with respect to the gap g. The resulting isolation makes it possible to tailor resonances over a wider range.

In embodiments, the device further comprises waveguides at least partly embedded, laterally, in dielectric structures, in which antennas of the pairs are also laterally embedded, at least partly. The present devices may notably be monolithically integrated with waveguides, as necessary to enable detection according to the present approach. The waveguides may for instance be plasmonic, dielectric or photonic waveguides.

For example, the device may further comprise, integrated therein, one or more of an electro-optical light source and an electro-optical light detector, coupled to a respective one of said waveguides. In particular, the light source and/or the light detector may advantageously be seamlessly integrated in the optical sensing device to enable very small form factors.

According to another aspect, the invention is embodied as an optical sensing system. This system comprises an optical sensing device such as described earlier, as well as an (external) electro-optical light source and an (external) electro-optical light detector. The light source and the light detector are configured for optically exciting the pairs of antennas and optically detecting signals therefrom, in a reflection, e.g., backscattering, geometry or in a transmission geometry.

According to a final aspect, the invention can be embodied as a method for optically sensing an analyte. Basically, this method comprises optically exciting the pairs of antennas of an optical sensing device such as disclosed herein, while letting an analyte reach electro-magnetic field enhancement volumes of the device, to concentrate electromagnetic radiation in such volumes. Concomitantly, optical signals as modulated and/or generated by the analyte in the volumes are optically detected, via the plurality of pairs of opposite antennas.

Different classes of optical sensing modalities can be contemplated. In one of them, the detection involves elastic or inelastic light scattering at the analyte by a combination of spectrally different field enhancements as obtained through the distinct pairs of antennas. Another sensing modality relies on detecting resonance shifts induced by the presence of an analyte bound due to receptor layers on the antennas, as made possible thanks to embodiments of the present devices.

Devices, apparatuses, systems and sensing methods embodying the present invention will now be described, by way of non-limiting examples, and in reference to the accompanying drawings.

BRIEF DESCRIPTION OF THE DRAWINGS

FIGS. 7A-9B depicts pairs of cross-sectional views, whose orientations are similar to those of FIGS. 3A and 3B, of an optical sensing system and sensing devices, according to further embodiments. Namely:

FIGS. 7A and 7B pertain to a sensing system with external light source and detector, in a reflection geometry;

FIGS. 9A and 9B depict another sensing device system, comprising integrated waveguides, an electro-optical light source and an electro-optical light detector, coupled to respective waveguides;

Figure 1A:
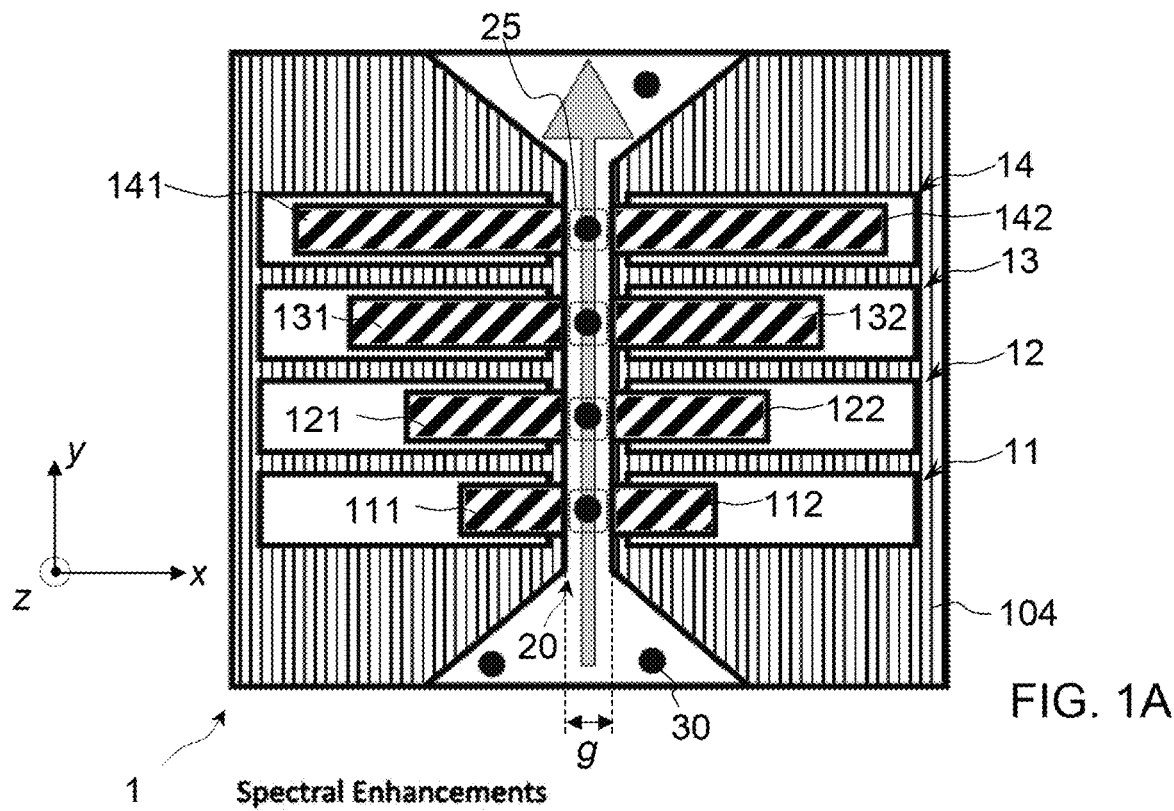
FIG. 1A is a top view of a sensing device, involving optical nano-antenna pairs along a channel, according to a first class of embodiments.

The accompanying drawings show simplified representations of devices, systems or selected parts and components thereof, as involved in embodiments. Technical features depicted in the drawings are not necessarily to scale. Similar or functionally similar elements in the figures have been allocated the same numeral references, unless otherwise indicated.

DETAILED DESCRIPTION

The following description is structured as follows. First, general embodiments and high-level variants are described (sect. 1). The next section addresses more specific embodiments and technical implementation details (sect. 2).

1. General Embodiments and High-Level Variants

In reference to FIGS. 1A, 2A, and 3-12, an aspect of the invention is first described, which concerns optical sensing devices 1, 1a-1n.

Such optical sensing devices comprise, each: a substrate 102; a first dielectric layer 104, which extends on this substrate 102; a second dielectric layer 204; and antennas 111-141; 112-142.

The term "antenna" as used herein refers to an optical device designed to receive and transmit electro-magnetic radiation ranging from the ultra-violet over the visible to the infrared frequency domain. Antennas as contemplated herein notably include optical antennas, plasmonic antennas, dielectric antennas, and electro-optical antennas, as well as sets and/or combinations of such antennas. In addition, an antenna in the present context does not necessarily need to be electrically driven or convert the incident electro-magnetic radiation into an electrical signal. Notably, such antennas can guide and concentrate electromagnetic radiation into near-field sub-diffraction volumes and couple light out into the far-field.

Figure 3A:
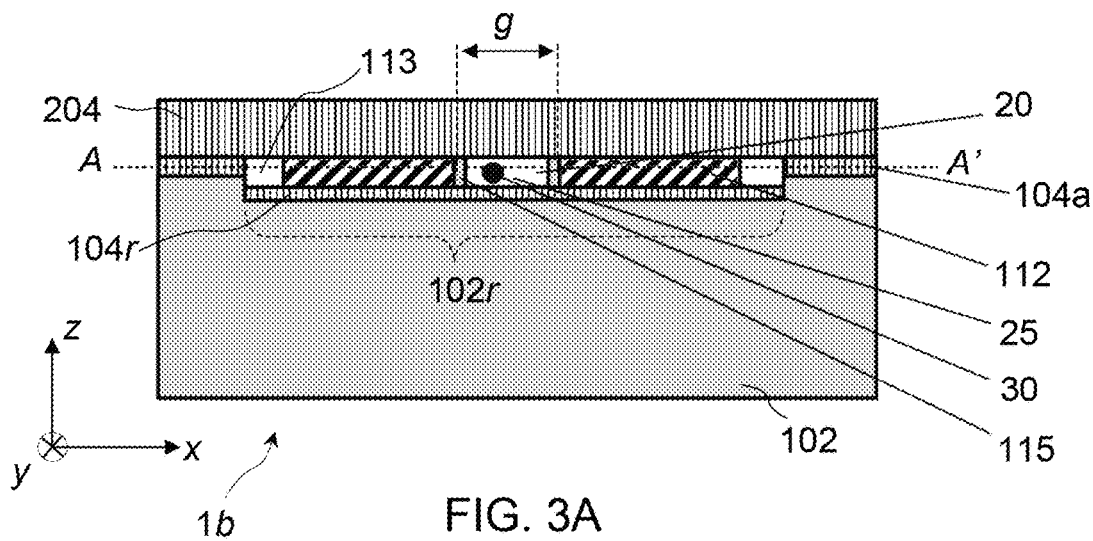
FIG. 3A is a 2D cross-sectional view of another sensing device (as otherwise shown in FIGS. 3B and 3C), the cross-section taken in the plane (x, z), at the level of the cutting plane B-B' shown in FIG. 3B.

Although termed 'layers', the dielectric layers 104 and 204 are not necessarily plane. For example, layer 104 may notably extend on a recess 102r of the substrate 102, so as to form a recessed portion 104r of the dielectric layer 104, on which antennas are arranged, as seen in FIG. 3A. Similarly, the antennas and the substrate may be structured. The materials used for the antennas may include, but are not necessarily limited to, metallic materials, semi-metallic materials, semiconducting materials, such as silicon (Si), poly-Si, amorphous-Si, or III-V compound semiconductors, dielectric materials, organic carbon-based materials, or 2D layered materials. The substrate 102 is preferably made of silicon, glass or quartz and the dielectric layers of oxides such as $SiO_2$.

According to the present inventive concepts, the antennas are arranged in a plurality of pairs 11-14 of opposite antennas 111-141; 112-142. It is worth mentioning that what is, here, termed a "pair of antennas", like antennas 111 and 112 in FIGS. 1-2, may in fact also be regarded as a single antenna, comprising two antenna elements, where two elongated elements (such as rods, spheres, discs, triangles) are oriented end to end on the same axis. In the present technical field, such a pair of antennas is interchangeably referred to as: a single antenna; a pair of antennas; a pair of antenna elements; a dimer antenna, a doublet, etc., or, still as an antenna. However, since each of the elements 111, 112, 121, . . . , 142 may, itself, behave as an antenna, we choose here to refer to a pair of antennas, it being understood that each pair comprises two elements, as consistently assumed in the present embodiments.

The antennas are patterned on the first dielectric layer 104. Opposite antennas are, in each of the pairs 11-14, separated by a gap g, which, on average, is between 1 nm and 50 nm. This gap is measured in the direction x, which, as indicated in the accompanying drawings, is parallel to the main plane of the substrate 102. The pairs 11-14 of antennas have different geometries, as explained in more detail below.

In addition, the second dielectric layer 204 covers all of the antennas, including the gaps defined between antennas of each pair. This way, the layer 204 defines, together with the antennas (and a layer underneath), a number of field enhancement volumes 25, which number corresponds to the number of antenna pairs. That is, an electro-magnetic field enhancement volume 25 is defined between opposite antennas of each pair 11-14, thanks to the gap g provided between opposite antennas. The device and, in particular, the antennas, are otherwise configured such that electro-magnetic radiation can be concentrated in each volume 25 accordingly defined. This, as we shall see, allows an analyte 30 to be optically sensed, via opposite antennas of each pair, in operation.

The gaps g, together with the thicknesses (measured perpendicularly to the substrate, along direction z) of the antennas and their apex (as measured parallel to direction y, i.e., parallel to the substrate and perpendicular to the direction x of extension of the gaps), impacts the dimensions of the field-enhancement volumes 25. On the one hand, one wants to minimize the gaps g, in order to minimize the sensing volume 25 and maximize the field-enhancement. Thus, the gaps g formed between antennas of each pair are here between 1 and 50 nm. Still, such gaps are preferably less than 20 nm, for reasons that will become apparent later. On the other hand, and as the present Inventors observed, having gaps g that are, each, less than 2 nm might substantially, if not strongly, limit the analyte throughput and may further lead to possible electron tunneling from one antenna to the opposite one, which is a detrimental effect if very high field enhancements are targeted. Thus, a preferred gap range is between 2 and 20 nm (note in passing that all intervals mentioned herein are closed intervals).

Depending on the applications sought, more preferred ranges for said gaps may for instance be of 2 to 5 nm, e.g., when sensing gaseous analytes, or of 10 to 20 nm, e.g., for sensing small biomolecules either in gas- or liquid-phase. Gaps of 20 to 50 nm may for instance be needed for sampling small droplets or larger molecules. Such gaps are preferably constant (they do not appreciable vary from one pair to the other, subject to ±0.1 nm, owing to the preferred fabrication methods contemplated herein) I.e., if a nominal gap g is, e.g., 5 nm, then gaps between antennas of each pair will all be between 4.9 and 5.1 nm.

The pairs of antennas differ, geometrically speaking. Preferably, all pairs differ, as assumed in FIGS. 1-2. Yet, not all of the pairs of antennas need be given a unique geometry (i.e., some of the pairs may be identical, some of them may differ in geometry). The antenna pairs may notably differ in length, as in FIGS. 1-2. Having different lengths of antenna pairs allows their optical resonances to be tuned, which, in turn, determines their electro-magnetic field-enhancement range, spectrally.

The number of antenna pairs 11-14 (e.g., forming a sequence along a same channel) will typically be between 2 and 20, although the upper limit is, in principle, not limited. A larger number of antennas, e.g., 1 000 or more, may be needed to allow the detection of diluted gases. For example, assume that the active volume of one antenna contains less than 10 molecules. If a gas to be sensed is in the ppm range, the chance of having a molecule of interest in the sensing volume is <1:100 000, which requires too long measurement times (e.g., 100 000 measurements). The number of measurements can nevertheless be reduced by the number of antennas: For 1 000 antenna pairs the time is reduced from 100 000 to 100. Another approach to reduce the number of measurements is to increase the dwell time in the active volume by reversible adsorption, preferentially with a specificity factor of 100-100 000. Too small specificity does not reduce the time sufficiently, too large specificity makes a molecule stick too long so that complex mixtures cannot be measured. It is also advisable to have antennas with specificity for different classes of molecules in the different parallel channels. To determine the concentration it is necessary to calibrate the selectivity of the surface treatment.

Figure 2A:
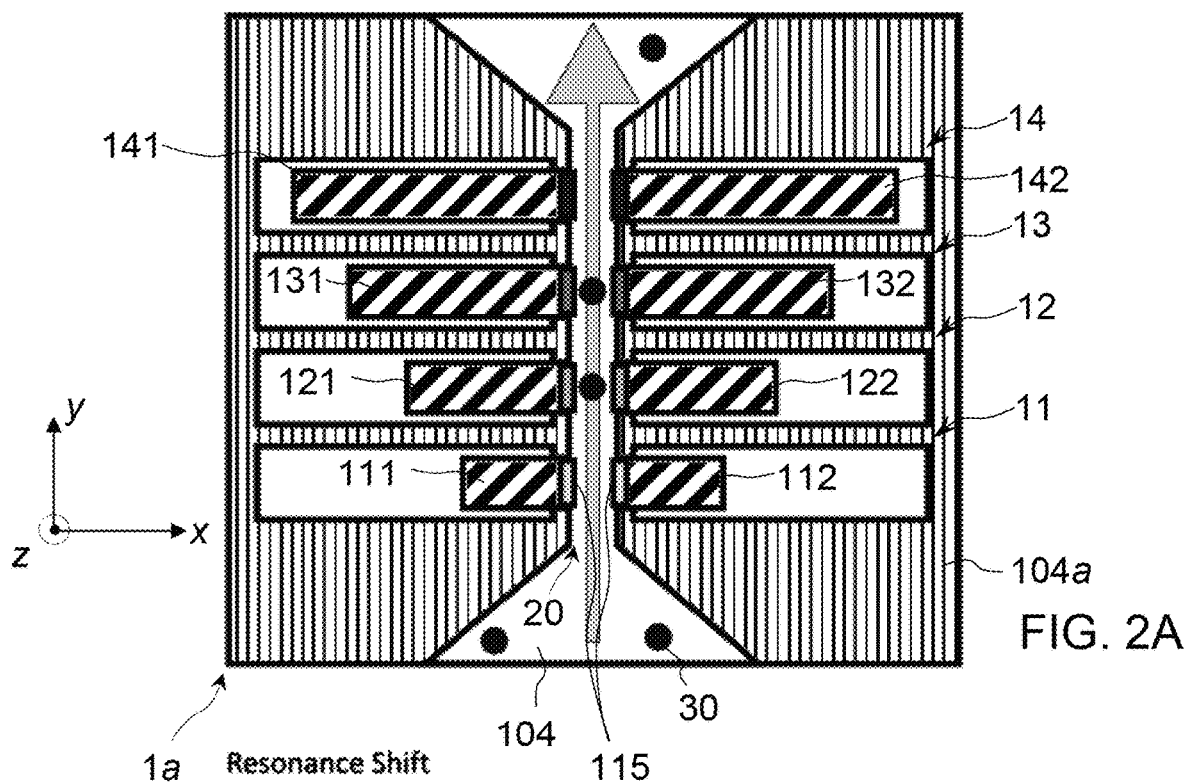
FIG. 2A is a top view of a similar sensing device, yet involving chemical receptor layers arranged on inner facets of opposite antennas, according to a second class of embodiments.

Note that the antenna pairs need typically not be specifically sorted along the channel with respect to their geometries (e.g., their lengths), contrary to what FIGS. 1A and 2A may suggest. The lengths of the antennas may nevertheless obey specific design rules, e.g., as imposed by the spectroscopy technique sought. In addition, for some applications, the number of antennas may be defined by the probing spot size or by the spectral range to be covered, in order to enable a given spectroscopy technique, e.g. Raman spectroscopy.

Present Inventors have developed fabrication methods that make it possible to achieve well-defined, nanometer-ranged gaps g between antenna elements. In particular, such fabrication methods are, here, exploited to obtain self-aligned antenna-channel structures. Thanks to the inverse patterning approach involved and the strategy chosen to maintain a buried channel material during all fabrication steps that may potentially alter the gap sizes, the dimensions of some key structures can be markedly reduced below the limiting fabrication feature sizes, to allow the desired field enhancement to be reached (e.g., using 1 to 50 nm gaps or, even, down to 1 to 20 nm, for extreme field enhancements). As a result, and owing to their very small dimensions, the field-enhancement volumes 25 formed between opposite antennas allow unprecedented concentration of electro-magnetic radiation. An example of a preferred fabrication method is illustrated in FIGS. 13A-13E; it is discussed in detail in sect. 2.

In addition, such fabrication methods make it possible for a plurality of antennas to be self-aligned with a common channel 25, to yield a device as depicted in, e.g., FIG. 1A or 2A. The channel 25 accordingly obtained makes it possible for analytes (e.g., molecules in gas or liquid phase) to be deterministically funneled into the field-enhanced regions 25 of the nano-antennas, where they can be detected through surface enhanced spectroscopies (e.g., surface-enhanced Raman, infrared absorption or fluorescence as well as intensity and phase changes based on optical resonance shifts).

As it will be realized, the present approach opens up a broad range of new measurement techniques and sensing modalities, which can be applied to very small quantities of analytes. Examples of such techniques are discussed in detail in section 2. In particular, they enable high integration densities and hyperspectral sensing modalities based on multi-resonance antennas, chiral field generation and loss suppression through exploitation of polarization. Additionally, the field enhancements and field gradients obtained thanks to the very small gaps g allow optical selection rules to be altered, whereby infrared-modes can be accessed through Raman spectroscopy, under the so-called field-gradient Raman conditions.

Moreover, optically non-interfering electrical gating capabilities, as enabled by the present devices, allow additional sensing modalities, analyte release functionality in case of active binding and thermal control of nano-chemical reactions by cooling and heating. All this is now discussed in detail, in reference to embodiments of the invention.

As illustrated in FIGS. 1A and 2A, the pairs 11-14 of antennas preferably have different lengths, as evoked above. Note that said lengths pertain to antenna pairs rather than to the antennas themselves. Said lengths are measured between outermost ends of the opposite antennas of each pair, along axis x. The length of an antenna pair defines the optical resonance for this pair. Thus, some or even all of the antenna pairs may advantageously have different lengths, to enable distinct types of measurements on the same substrate. Still, other geometric factors may be varied, independently from or together with the lengths of the antenna pairs, e.g., in order to be able to further tune the optical resonances.

For example, differences between the antenna pairs may involve asymmetries with respect to a center of the gaps g or a main axis of the antenna pairs, as measured along axis x or y, or, still, concern the orientations of the antennas with respect to an intended polarization state of the incident field. As the one skilled in the art will appreciate, other differences can be contemplated.

Beyond differences between the antenna pairs, also the antennas within each pair may differ. For example, opposite antennas within a given one (or more) of the pairs 11-14 may have different lengths (as measured along direction x). More generally, antennas may have distinct geometries, even within a pair. Having asymmetric antennas (with respect to the gap g along the axis y) allow more flexibility for tailoring the resonances and higher order charge distributions. Notably, this makes it possible to further tune the optical resonance and, this, over a wider range, e.g., when relying on high-order or non-linear modes. Furthermore, asymmetric antennas can be tailored to harness specific polarization states of the incident light (e.g., circularly polarized or azimuthally polarized light).

In simpler variants, however, the antennas may be symmetrically shaped with respect to the axis y of the channel and, this, possibly in each of the pairs 11-14, as assumed in FIGS. 1-9. Doing so might ease the fabrication process, though the preferred fabrication methods described in sect. 2 allow, in principle, arbitrary shapes to be created with self-aligned channel-antenna.

In general, the antennas may have a form factor. For example, in the embodiments of FIGS. 1-3, 4A-4B, the antennas of the pairs 11-14 have a form factor, such that their largest dimension is parallel to the direction x. Such a form factor makes it easier to achieve resonance shifts, which lead to measurable changes in the scattered/transmitted intensities of the antennas.

More generally though, the antennas may be shaped in various geometries, as illustrated in FIG. 6. Antennas may be shaped as, e.g., rods, spheres, triangles, bowties, etc., or be tapered, straight, or curved, etc. I.e., each antenna element 111, 112, 121, . . . 141 may be a more or less symmetrical object per se, just like each pair 11-14 of antenna elements may be more or less symmetric with respect to the gap g.

As discussed earlier, the intra-pair gaps g enabled by the preferred fabrication methods allow very small field-enhancement volumes (small mode volumes) 25 to be achieved. Quantitatively, the volumes 25 defined between the antennas of each of the pairs 11-14 shall preferably be, each, between 1 $nm^3$ and $10^5$ $nm^3$. This stems from the fact that the thickness and the depths of the antennas may typically be between 1 to 50 nm. Thus, on the smaller end, a volume of approximately 1 $nm^3$ may be achieved, assuming a 1 nm gap g (measured along axis x), an average thickness of 1 nm for the antennas (measured along z), and an average antenna apex of 1 nm (measured along y). On the higher end, a volume of approximately $10^5$ $nm^3$ may possibly be achieved, assuming a 50 nm gap×50 nm thicknesses× 40 nm width. Of course, any intermediate range can be contemplated, in applications.

As it may be realized, such volumes (i.e., $10^{-24}$ to $10^{-19}$ liters) allow extreme field intensity and field gradient conditions to be achieved, in operation. Such gradients are for instance sufficient to change the optical selection rules in scattering processes, enabling simultaneous detection of infrared modes in addition to Raman modes. Embodiments of the present invention may therefore be exploited to drastically broaden the current approach to spectroscopy. Indeed, dimensions that may here be achieved for the sensing devices make it possible to provide comprehensive information, in a single experiment, with single-molecule sensitivity. The extreme field/gradient conditions enabled in embodiments may thus be used in devices such as sensors with embedded nano-channels, e.g., for gaseous analyte detection in environmental monitoring. Sensors may for instance be achieved that can be used for biomarker detection in exhaled breath analysis, or in other applications in molecular sensing, where self-aligned channels for gas or liquid media are used for optimized interactions between high-field regions and an analyte-containing medium. The present devices and techniques will also prove advantageous for surface-enhanced Raman spectroscopy (SERS), as further discussed in sect. 2.

In the embodiments illustrated in FIGS. 2 and 3, the optical sensing devices 1a, 1b further comprise chemical receptor layers 115. The layers 115 are oppositely arranged on opposite, inner faces of opposite antennas of each pair 11-14. Providing chemical receptor layers 115 makes it possible for the antennas' ends to selectively bind specific types of analytes. In variants, only a subset of the antenna pairs are provided with chemical receptor layers. In other variants, subsets of antennas are provided with distinct types of chemical receptor layers. In all cases, suitably chosen receptor layers allows control over the binding properties of analytes on specific antenna pairs. In further variants, the bulk of the antennas may be made of different materials, so that analytes may selectively be bonded, directly on the antennas' inner faces (no chemical receptor layer is needed in that case).

Using chemical receptor layers may be required in some applications, e.g., relying on optical resonance shifts rather than direct spectroscopic probing, as further discussed in sect. 2. However, chemical receptor layers 115 are not always required, for example when directly probing Raman vibrations, which provide a unique fingerprint of each molecular compound (see sect. 2).

As evoked earlier, the present devices preferably comprise one or more channels 20, the latter configured so as to link several field-enhancement volumes 25. For example, in embodiments as illustrated in FIGS. 1A, 2A, and 10-12, the sensing device 1, 1a-1n comprises one or more channels 20. Opposite antennas 111-141; 112-142 in each pair 11-14 (of a given set of pairs) are arranged, in vis-à-vis, along a channel 20 (or along a portion thereof). In general, the antennas may be placed outside, inside or within the channel. As assumed in FIGS. 1A, 2A, and 10-12, a channel is otherwise configured so as for several field enhancement volumes 25 (as defined between opposite antennas) to be in fluid communication, whereby a gas or liquid flow of analyte may pass from one volume 25 to the other.

In other words, the gaps g define channel sections, between which flow communication is ensured, thanks to other, intermediate portions of the channel 25. As evoked earlier, such a channels can be configured so as to allow analyte delivery and funneling along the antenna pairs, for the analyte to interact with the electro-magnetic fields in the enhancement volumes 25.

Larger gaps and channel dimensions, combined with parallelization of the channels (as in FIGS. 10-12) allows higher mass flow throughput to be obtained, which can be helpful to increase the dynamic range of the sensor in terms of its sensing volume per time unit. Note that, even though the field enhancements are not as strong anymore at separation distances of more than about 50 nm (compared, e.g., to those obtained with gaps less than 10 nm or 20 nm), a change in the dielectric environment in the gap may nevertheless appreciably shift the optical resonance and thus become detectable with simpler detection modalities than the spectral high-resolution Raman signal detection's.

The examples of FIGS. 1-9 depict, each, a device comprising a single channel. This channel 20 extends generally along a direction y (parallel to the main plane of the substrate and perpendicular to direction x). The examples of FIGS. 10-12 involve several channel sections, which communicate. The sections of the channels along which antennas are oppositely arranged are straight, similarly to the channel 20 shown in FIGS. 1-9. More generally though, the channels (or channel sections), along which antennas are oppositely arranged, need not be straight.

The intra-pair gaps g (along axis x) have been discussed in detail earlier. In the following, additional considerations as to the inter-pair separations are given. The inter-pair separations between contiguous pairs 11-14 of antennas, i.e., are measured along the direction y of the channel. As for example seen in FIGS. 1A, 2A, opposite antennas 111-141; 112-142 of each pair 11-14 are patterned along a section of the fluid channel 20 that extends parallel to the direction y.

The minimal, inter-pair separation is preferably of at least 1 nm. Yet, several cases may be distinguished. For antennas with large electronic cross-talk, a small inter-pair separation of at least 1 nm will typically be desired, to enable electron exchange. For antennas with large optical cross-talk, separations of 1-50 nm would likely be preferred, to enable strong optical coupling. For antennas with negligible electronic cross-talk, a separation of at least 20 nm is typically required, whereas for antennas with negligible optical cross-talk, typically a separation of at least 100 nm is required if excited in the near field or 1 µm if excited from the far field (due to the diffraction limit).

Figure 1B:
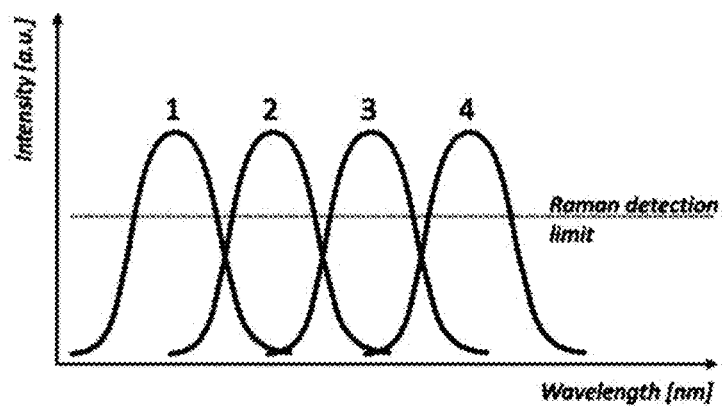
FIGS. 1B and 1C are graphs illustrating a detection scheme based on hyperspectral field enhancements, which allows the Raman detection limit for single analytes to be overcome.
Figure 1C:
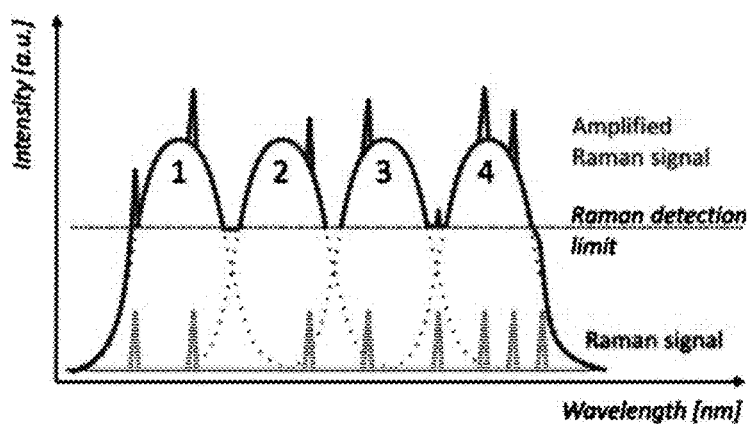

A sufficient separation may for instance be desired to avoid inter-pair tunneling/crosstalk effects, e.g., when performing Raman signal detection (see FIG. 1C). However, densely packed antenna pairs with inter-pair tunneling/crosstalk may not be an issue or, even, desired for some types of detection, e.g., mere Raman signals measurements, to achieve a very homogenous field enhancement performance, based on hybrid resonances, for example. In that case, the response of the sensor has to be calibrated to account for the more complicated enhancement spectra.

In the following, preferred implementations of the antennas are discussed, where antennas are embedded in dielectric structures. In particular, and as seen in FIGS. 1A, 2A, 3A-3C, and 4-6, the antennas may be at least partly embedded, laterally, in a dielectric structure 104a. The dielectric structure 104a may notably be shaped so as to define lateral walls for the channel 20. Such lateral walls extend transversely to the main plane (x, y) of the substrate.

Figure 3B:
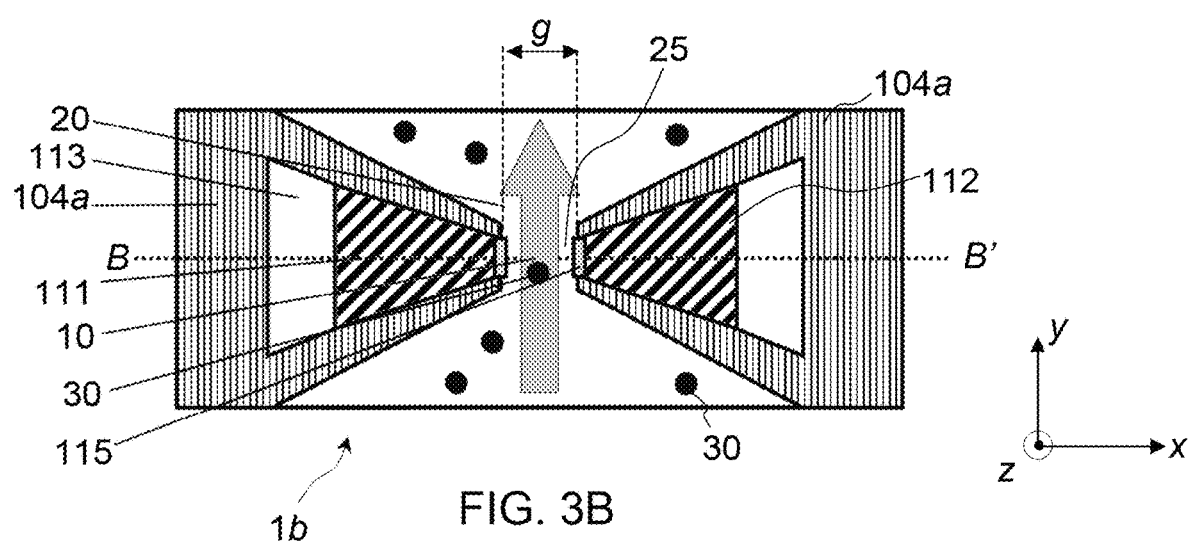
FIG. 3B shows a different cross-section (as viewed from, e.g., the top), in the plane (x, y), at the level of the cutting plane A-A' shown in FIG. 3A.

As seen in FIG. 3A-3B, lateral embedding may for instance be achieved by patterning a first layer 104, which initially extends above and covers a recess 102r performed in the substrate 102. The embedding structures 104a eventually obtained may thus be residual portions of outer portions of the first dielectric layer 104. In general, the boundaries of both the channels and the antenna may result from a same patterning step, performed on an initial layer 104, as discussed later in more detail. In variants (not shown), the embedding structure(s) 104a may be patterned (at least partly) from an intermediate dielectric layer, deposited between the initial layers 104 and 204. Yet, the intermediate dielectric layer may be of the same dielectric material as layers 104 and 204.

Preferably, lateral portions of the embedding structures 104a are tapered, as seen in FIGS. 1-9. This favors the insertion and the propagation of the analytes in the channels 20 and avoids clogging of analytes molecules. If necessary, filtering elements may be placed into the funneling region, to avoid clogging. In all cases, one may further seek to achieve lower pressure conditions in regions outside the field-enhancement volumes or the channels, to favor the propagation of analytes.

Figure 4A:
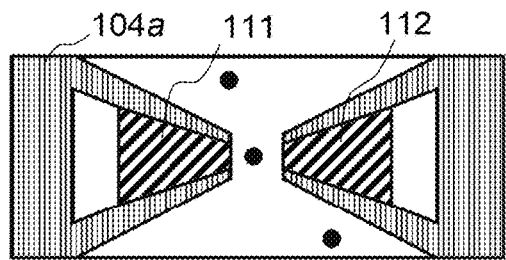
FIGS. 4A-6B shows cross-sectional views, similar to FIG. 3B, of devices having different antenna geometries, namely with antennas located outside the analyte-delivery channel (FIGS. 4A, 4B), along the channel (FIGS. 5A, 5B) or inside the channel (FIGS. 6A, 6B), according to further embodiments.
Figure 4B:
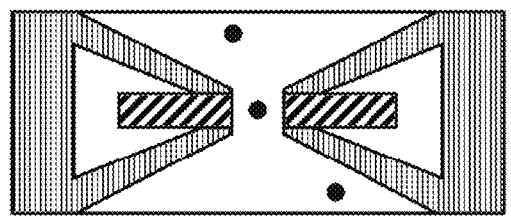
Figure 5A:
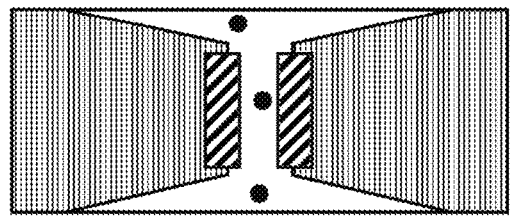
Figure 5B:
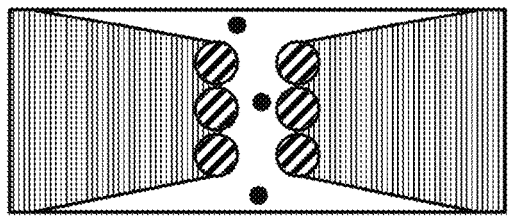
Figure 6A:
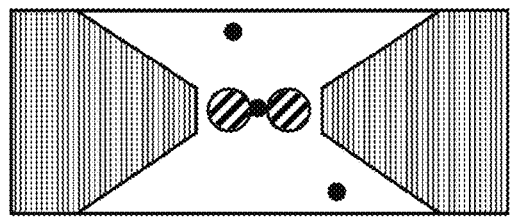
Figure 6B:
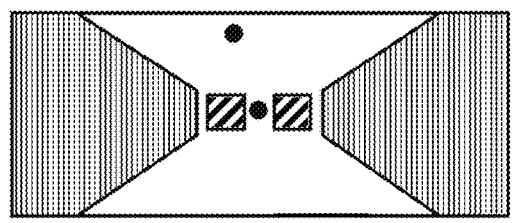

Examples of laterally embedding structures are shown in FIGS. 4-5, together with different designs of antennas. In variants, the antennas may be arranged inside the channel, i.e., in the vicinity of tapered dielectric structures, yet without being embedded therein, as illustrated in FIGS. 6A-6B. In principle, such variants could be seen as advantageous as they make it possible to de-couple the antennas from the surrounding structures, a thing that a priori benefits their optical properties (it reduces damping). However, such variants may potentially allow clogging of analytes due to the voids between antennas and the lateral, dielectric structures. To prevent this, structures as depicted in FIGS. 4 and 5 can be adopted. Still, structures as shown in FIGS. 4A and 4B are preferred, because of the voids 113, which allow to partly de-correlate the laterally embedded antennas from their environment.

Depending on the properties sought for the devices, not all antennas (along a given channel) may need be embedded in a dielectric structure 104a. Thus, in variants, only a subset of the antennas can be laterally embedded in a dielectric structure.

Figure 3C:
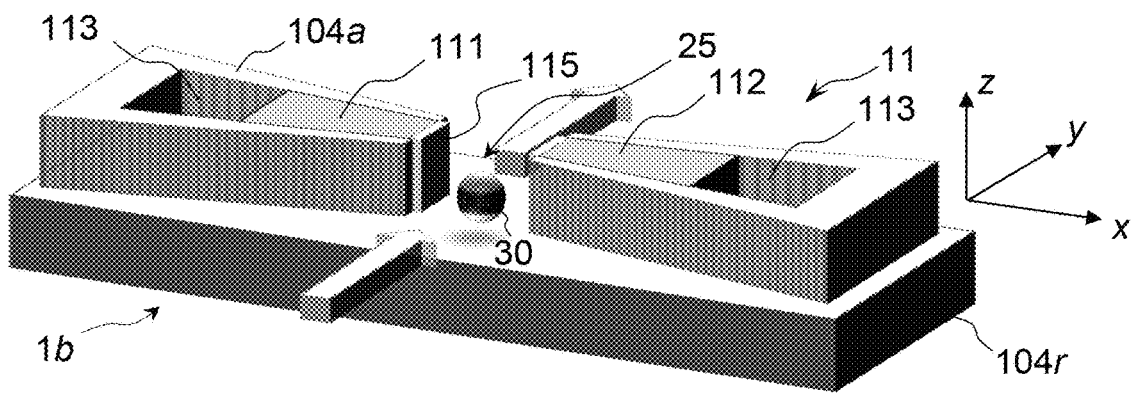
FIG. 3C is a 3D view of the same device (only the region about a single antenna pair is depicted in each case). Antennas are embedded in lateral, dielectric structures, wherein a void is provided at outermost ends of the antennas, according to embodiments.

In the embodiment of FIG. 3A-3C, the optical sensing device 1b has a substrate 102 that comprises a recess 102r, over which the first dielectric layer 104 extends. Thus, a recessed portion 104r of the first dielectric layer 104 is arranged on the recess 102r, whereas a peripheral portion 104p of the first dielectric layer 104 extends over a peripheral region of the substrate 102, around the recess 102r. The portion 104r is recessed from the peripheral portion 104p in the direction z. There, each antenna 111, 112 is patterned on the recessed portion 104r of the first dielectric layer. The peripheral portion 104p is further patterned so as to form the dielectric structure 104a, in which the antennas 111, 112 are partly embedded, laterally. Relying on a recess 102r is advantageous as it allows chemical mechanical processing on top with a well-defined stopping layer to terminate the planarization step, but is not a strict requirement.

As further seen in FIG. 3, the antennas may only be partly embedded, laterally, in the surrounding dielectric structure 104a, thanks to voids 113 defined in a peripheral region of the antennas, i.e., between an edge of the antennas and a portion of the neighboring dielectric structure 104a. This way, antennas can be partly isolated from the surrounding structures 104a. The voids 113 may for instance be defined at outermost ends of the antennas, with respect to the gap g separating them.

The optical sensing devices 1j, 1k depicted in the embodiments of FIGS. 8A-9B additionally include waveguides 114, 114a, which are also embedded (at least partly), laterally, in dielectric structures. The structures in which the waveguides are embedded may be patterned from the same layer 104 that otherwise serves to create lateral embedding structures 104a for the antennas.

Figure 8A:
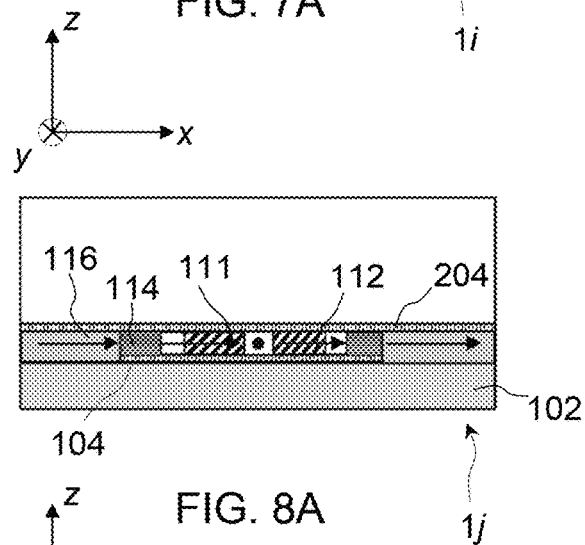
FIGS. 8A and 8B show a sensing device system, comprising optical waveguides and optical fibers integrated therein.
Figure 8B:
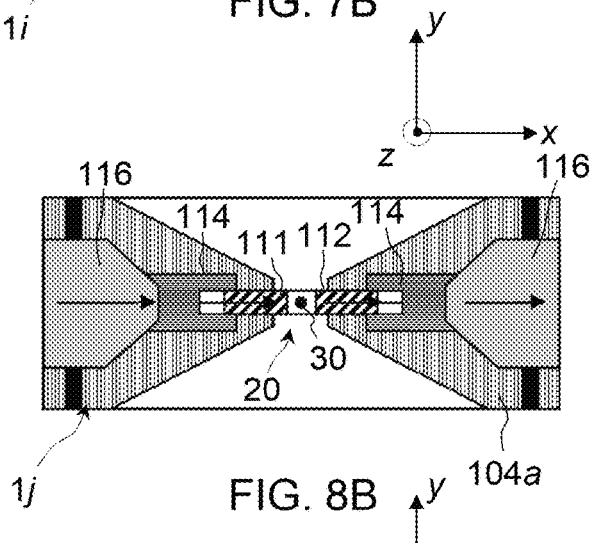

The waveguides may notably be optical waveguides 114, as assumed FIG. 8. Yet, more generally, plasmonic, dielectric or photonic waveguides 114, 114a may be contemplated. For example, optical waveguides 114 can be configured for coupling electromagnetic radiation into and/or from the antennas 111, 112. The optical waveguides 114 may for instance be coupled to outer optical fibers 116. The latter may possibly be partly embedded in the same dielectric structure 104a, laterally, in which the antennas and waveguides are otherwise laterally embedded. Waveguides are typically designed to optimize the confinement and propagation length of optical modes. In addition, the present devices may involve light sources 117 and detectors 118, as assumed in FIGS. 8-9, and as necessary to enable detection according to the present principles.

Figure 9A:
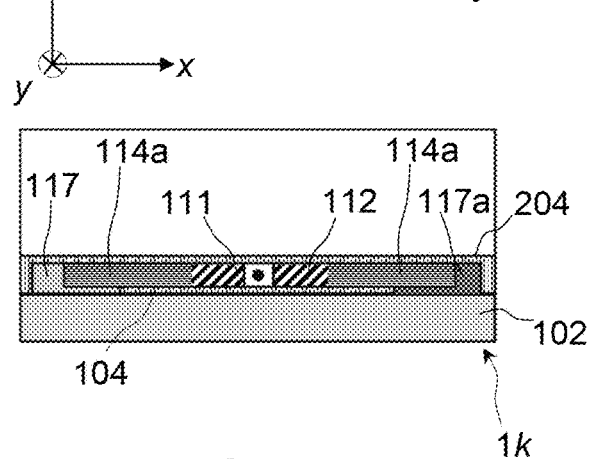
Figure 9B:
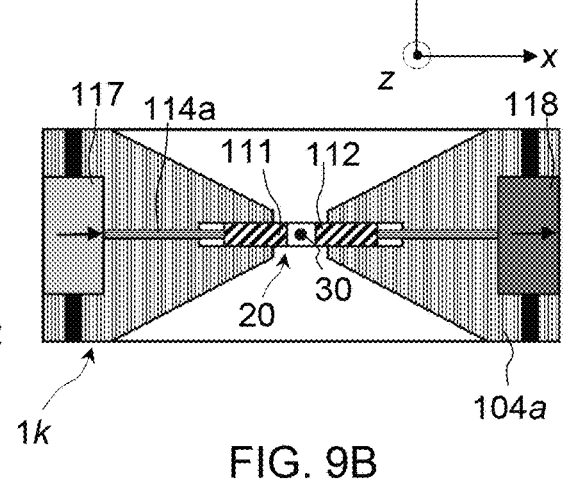

For example, in the embodiment of FIGS. 9A-9B, the optical sensing device 1k includes waveguides 114a, an electro-optical light source 117 and an electro-optical light detector 118, wherein the light source and the detector are, each, coupled to a respective one of the waveguides 114a. All components 114a, 117, 118 can be integrated, e.g., monolithically integrated, in the device, as made possible by the preferred fabrication processes.

In that respect, it will be appreciated that designs and fabrication methods disclosed herein are compatible with a monolithic integration of silicon, III-V semiconductor materials, dielectric materials and metals (in particular plasmonic materials). In variants, only a subset of the components 114, 116, or 114a, 117, 118 may be integrated in the sensing device. For example, the light source 117 and the electro-optical light detector 118 of the sensing device 1k depicted in FIGS. 9A-B are, each, monolithically integrated in the device 1k.

Figure 7A:
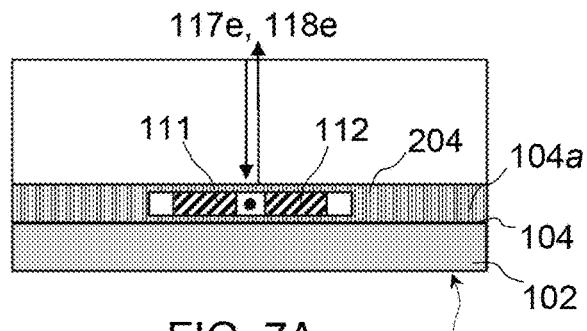
Figure 7B:
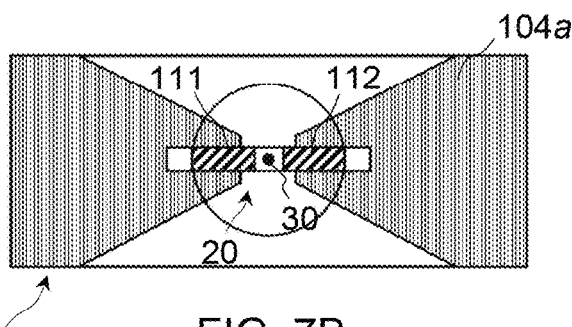

In variants, one may use an external light source and detector, which together with a sensing device as depicted in FIGS. 7A-7B, form a sensing system 1i, according to another aspect of this invention. The optical sensing system 1i depicted in FIG. 7 comprises an optical sensing device as described earlier (yet free of light source and detector), as well as an electro-optical light source 117e and an electro-optical light detector 118e. The light source 117e and the detector 118e are typically arranged in transmission geometry. They allow for optically exciting the pairs 11-14 of antennas and optically detecting signals modulated or, even, generated by analytes in the cavity 25.

Next, according to a final aspect, the invention can be embodied as methods for optically sensing analytes, in a sensing device such as described above. General aspects of these methods have already been described earlier, be it implicitly. Essentially, in such methods, an analyte is introduced, e.g., using active pumping means, capillarity, pressure difference, or diffusion, in the field enhancement volumes 25 of the optical sensing device, while optically exciting the pairs 11-14 of antennas of this device, to concentrate electro-magnetic radiation in these volumes 25. Meanwhile, optical signals as modulated and/or generated by the analyte in the volumes 25 are optically detected, via the plurality of pairs 11-14 of opposite antennas.

Several techniques can be contemplated, as explained in detail in the next section. One approach (FIGS. 1A-1C) relies on combining spectrally different field enhancements as obtained thanks to the pairs of antennas. E.g., the detection scheme may be based on hyperspectral field enhancements, to overcome the Raman detection limit for single analytes thanks to a strong field enhancement.

Another approach (FIGS. 2A-2C) makes use of a device such as depicted in FIG. 2A. Here, optical resonance shifts as induced by the presence of analyte bound due to the receptor layers 115 are detected. I.e., the analyte changes the dielectric environment or the dielectric properties of the gap, which induces optical resonance shifts of the entire antenna pair. Multiple antennas help to enable simultaneous measurements at different wavelengths, either to increase signal per time unit and optical excitation and probing spot size or to gain additional information for analytes with strongly dispersive dielectric function, e.g. metals.

In each case, one may further rely on reflector structures (dielectric or metallic), located above or below the antennas, laterally around them to allow more efficient readouts from the far field or improve coupling of incident/scattered/emitted light to waveguides or to increase the sensitivity, through increased photon-antenna interaction. Thus, the present sensing systems may include additional reflectors or directional elements.

The above embodiments have been succinctly described in reference to the accompanying drawings and may accommodate a number of variants. Several combinations of the above features may be contemplated. Examples are given in the next section.

2. Specific Embodiments—Technical Implementation Details

In the following, sensing devices and systems, method of fabrications thereof, and sensing methods are described in detail. In particular, it is shown how embedded and self-aligned channels can deterministically funnel analytes into field-enhanced regions of nano-antennas, where they can be detected through surface enhanced spectroscopies. Amongst other applications, such devices and techniques allow wide energy-range Raman spectroscopy to be conducted on the few-to-single molecule level, by combining deterministic analyte delivery into field-enhanced nano-volumes, through the use of optical nano-antennas with self-aligned channels.

2.1 Preferred Methods of Fabrication of the Optical Sensing Devices

2.1.1 General Aspects of the Preferred Fabrication Methods

The preferred fabrication methods are based on an inverse patterning approach (also referred to herein as "pattern-first approach" or "negative template approach"). The fabrication procedure combines lithographic patterning, cycled etching, molding or overgrowth, selective removal of excess material and buried material, to release a buried channel.

A key point of such methods is to manufacture suitable gaps, between opposite antennas of each pair. To that aim, a template structure is formed on a substrate, whose dimensions are reduced, as needed to achieve the nanoscale range. Then, an active material layer is deposited conformally on the substrate and on the template structure, so as for the active material layer to cover at least top and side surfaces of the template structure. Then, the active material layer is planarized and overgrown by a cover layer. One selectively removes the buried template structure with respect to the active material layer and the substrate. This way, ultra-narrow gap structures can be fabricated.

This approach allows a number of active-material post-growth or post-deposition treatment steps, such as annealing, yielding vertical side-walls with low line-edge roughness, as well as low roughness of both top and side surfaces of a metal film or improved morphologies. This is made possible thanks to the buried channel material that remains buried, acting as a spacer, throughout all fabrication and post-growth steps. Additionally, this process allows for self-alignment of feeding- and analyte-guiding structures as well as fabrication of electrical, electro-optical, all-plasmonic, all-optical and photonic devices.

By patterning a sacrificial channel layer, the complement of a gap can be fabricated using highly developed processes as available for silicon, yielding structures with vertical sidewalls and low line-edge roughness. These structures can further be reduced in size using approaches such as cycled oxidation and oxide removal, allowing for extremely precise control over dimensions below the feature sizes of lithography By depositing an active material layer in a subsequent step, methods such as epitaxial deposition or bottom-up seed-mediated growth, may be applied to obtain materials with the desired properties and allowing for post-growth treatment procedures, such as annealing and recrystallization. Chemical mechanical polishing or mechanical polishing is employed to remove the excess material on top of a resulting gap structure, significantly decreasing the top-surface roughness of the active layer and separating the antenna into halves. In a next step, the buried template including the antenna halves is covered by a cover layer. Then, the buried template is selectively removed, using, for example, etching, leading to the desired geometry with unprecedented active-material quality regarding gap sizes, surface roughness and morphology achieved by using the buried template structure as a spacer element throughout all relevant process steps including post-growth and post-deposition treatments.

By covering a structure with oxide and pattering openings before etching the silicon, buried channels leading perfectly through the feed gaps of optical structures can be obtained as the active layer and the channel are self-aligned with respect to each other. As a result, such methods allow the fabrication of sensing devices such as described in sect. 1. Furthermore, such fabrication methods allow for the fabrication of low-loss electro-optical and photonic devices by inverse patterning of active structures, and combining it with, for example, waveguides, modulators etc., which are suitable for direct and quasi-monolithic co-integration of miniaturized electro-optical and photonic devices with conventional semiconductor electronics for computing or silicon photonics for long-range transmission.

2.1.1 Detailed Example of a Preferred Fabrication Method

Basic steps of an example of fabrication process are now described in reference to FIGS. 13A-13F.

First, a substrate 102 is provided, which has a recessed portion. A dielectric layer 104 coats its top surface. Sacrificial complements 106 of the desired structures (called "buried template") are patterned onto a region that will later correspond to the desired channel, see FIG. 13A.

Figure 13A:
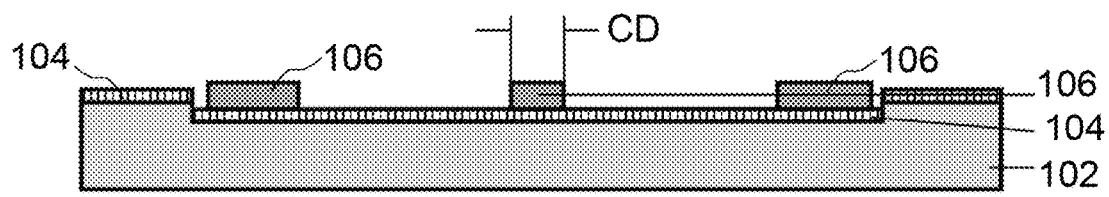
FIGS. 13A-13F depict cross-sectional views of a sensing device at various stages of its fabrication, using preferred fabrication methods.
Figure 13B:
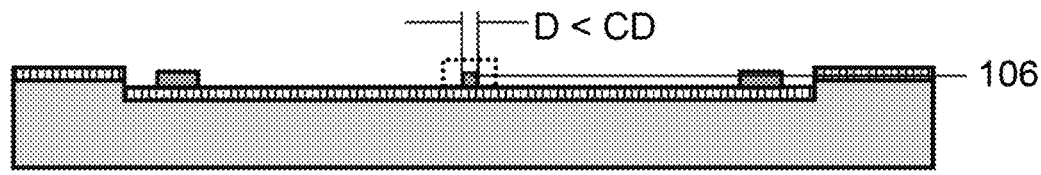
Figure 13C:
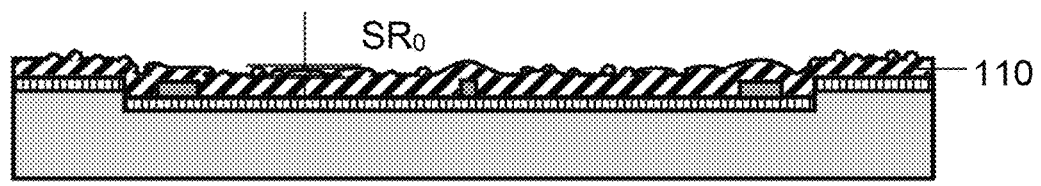

The initial fabrication resolution CD of the buried template is reduced down to nanometer dimensions, by selective etching, see FIG. 13B.

On top of the buried template, a second material 110 (referred to as "active material" above) is deposited (FIG. 13C) such that the active material conformally covers the buried template. A given surface roughness $SR_0$ is observed.

Figure 13D:
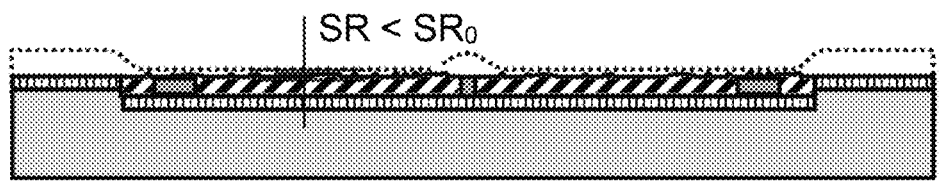

Chemical-mechanical polishing is employed to remove the excess active material 110 and to create separate structures 112 for the active material, thanks to the complement structures 106 previously reduced (FIG. 13D). The surface roughness is accordingly improved ($SR \ll SR_0$).

Figure 13E:
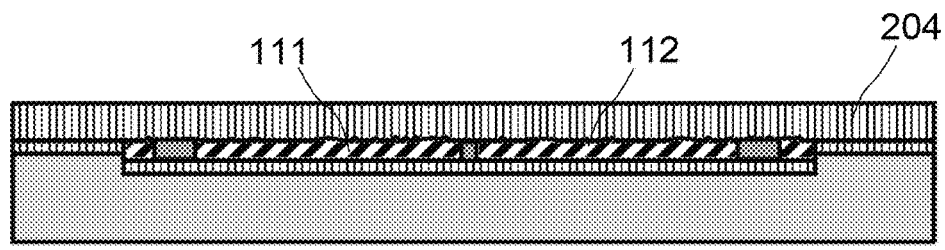

The planarized structure 110 is then coated entirely by an additional oxide layer 204, deposited on top (FIG. 13E).

Figure 13F:
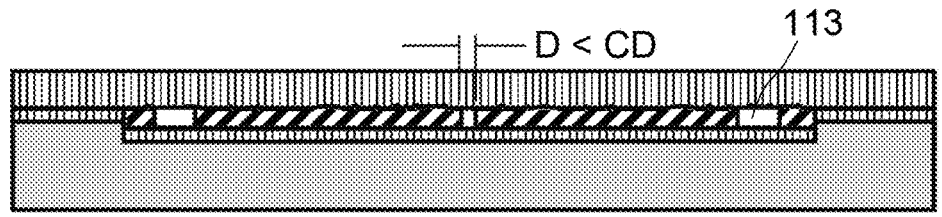

The buried template is finally selectively removed with the desired structures 112 of active material remaining, as previously defined by the reduced buried template (FIG. 13F).

Based on the above approach, more complex optical circuits can be fabricated, which involve components as discussed in the following sub-section.

As seen, only a few fabrication steps are needed, which involve common processing techniques compatible with CMOS-technology. They do not require exotic or expensive materials and, yet, allow unprecedented fabrication and alignment accuracies to be achieved, with high and reproducible field-enhancement for sensing.

2.2 Basic Components of the Devices

We assume that the sensing device comprises a plurality of antenna pairs and embedding structures, each as depicted in FIGS. 3A-3C (subject to optional chemical receptor layers 115 and voids 113). Additional features (e.g., the inter-pair channel 20) of this device are otherwise assumed to be similar to those depicted in FIG. 1A or 2A. This device comprises:

A plurality of pairs of nano-antennas, of defined geometries (bowties, rods, discs etc., which need not stringently have the same geometries) and materials (e.g., metal, highly doped semiconductors, high-index dielectrics, 2D layered materials, not stringently the same), with each component possibly divided into multiple material segments;

An electro-magnetic field enhancement (FE) mechanism, configured to generate a so-called field-enhanced "hot-spot" volume 25, wherein electro-magnetic radiation can be concentrated;

A channel 20 enabling analytes to be transported, deterministically, in either gaseous or liquid phase (or phase mixtures) into the field-enhanced volume;

Optionally, chemical receptor layers 115 are provided on antennas' inner faces, to bind only to specific types of analytes; and Optionally, void 113 are provided, to partly insulate the antennas and thereby improve the FE mechanism.

2.3 Principles of the Preferred Sensing Techniques

2.3.1 Background

The electromagnetic field of light incident on a conductor drives the mobile/free charge carriers of the conductor into coherent oscillations, i.e., surface plasmon polaritons (SPP). These oscillations lead to a strong confinement of electro-mechanical energy near the surface of the conductor, enabling concentration and guiding of light below the diffraction limit. Coupling of SPPs between multiple structures gives rise to extremely high local field enhancements (with local field strengths exceeding 100 times the incident field) in the small gap in between them. Similarly, in dielectric/hybrid structures, light can be strongly concentrated in gaps through induced charges and interference effects. Such regions of strong field enhancements ("hot-spots") are particularly beneficial for effects whose strength increases non-linearly with the field amplitude, such as surface-enhanced fluorescence, infrared absorption and Raman scattering. The antenna assists both in coupling light into the sensing volume, as well as in transducing the signal towards a detector. Specific antenna geometries further help to control the direction of the emission.

Molecular compounds ("analytes") 30 present in the hot spots experience drastically enhanced electro-magnetic fields and large field-gradients, potentially leading to the following effects:

Strong field enhancements, which, as Inventors observed, enable measurement of the Raman spectrum of a single molecule;

An optical resonance shift, due to local (near)-linear changes in the dielectric environment;

Strong field gradients enable usually forbidden infra-red (IR) modes to become emissive due to a change of the optical selection rules (originating from a change of the local, chemical bond specific chemical polarizability), leading to the so-called field-gradient Raman effect;

Surface enhanced florescence emission and fluorescence activation;

Surface enhanced infrared absorption for direct detection in the infrared region; and Further linear and non-linear effects ($2^{nd}$ and $3^{rd}$ harmonic generation, four wave mixing, antenna-molecule hybridization effects), so far mainly unexplored.

Based on these considerations, present Inventors have devised novel devices and methods, which make it possible to bring analytes 30 into FE hot-spots 25, in a well-defined, deterministic way and to apply sensing mechanisms that may rely on one or more of the above effects.

2.3.2 Preferred Mechanisms

The following describes how the patterning of self-aligned channels in nano-antennas can be employed to create sensing devices. In particular, it describes in detail how geometry and polarization can be used to tailor spectrally and spatially emission characteristics and near-field distributions. It is further described how the antennas can be integrated in systems with enhanced functionalities such as multi-modal sensing devices using electrical contacts or antenna encapsulations, in order to avoid quenching of the light emission.

Two detection schemes are now described proposed, which are based on physical mechanisms described in sect. 2.3.2.1 and 2.3.2.2.

2.3.2.1 Detection Mechanism Based on Field Enhanced Non-Linear Spectroscopies A first detection mechanism combines spectrally different field enhancements, tailorable through the antenna geometries. The resonances of the nano-antennas can be tailored, based on their shapes and sizes (FIGS. 1A-1C), resulting in spectrally different field-enhanced regions.

As non-linear processes, fluorescence, infrared absorption and Raman scattering require a certain field enhancement to become detectable over linear detection processes and detector noise. The spectral enhancements of the array of antennas can be tailored such that their FE bands create wide-energy field enhancements for broadband spectroscopy. At the same time, the spatial distribution of the near-field enhancement can be engineered well below the diffraction limit, enabling simultaneous sensing at multiple locations (still within the excitation spot size). This, in turn, makes it possible to achieve enhanced time resolution, multi-analyte detection and enhanced packaging densities of sensing elements.

Through resonant enhancement, the signals due to analytes passing the different FE hotspots become detectable. For example, the scattered, emitted, transmitted or reflected light can be collected and analyzed, e.g., thanks to an external detector combined with a high-resolution grating. Overall, an amplified field-enhanced spectrum results, over a wide energy range (ideally from ultraviolet [UV] to near IR and full IR). The antennas can be densely packed such that within one excitation hotspot (typically 1 µm) all antennas are excited simultaneously as the scattered/emitted signal is collected.

The typically broad resonances of optical antennas (FWHM of 100-200 nm) provide spectrally well-defined field enhancement regimes. Sharper spectral features compared to the normal dipolar resonance profiles can be achieved through interaction of quadrupolar and dipolar modes, employment of Fano resonances and/or through excitation of sub-radiant modes. Such resonance narrowing approaches enable only certain specific spectral regions to be enhanced or specifically probed, which is favorable where simpler detection mechanisms than spectrometers are used, e.g., integrated photodiodes with narrow band-pass filters.

Notably, the same FE-based detection principle can be applied to also detect Raman scattering at IR-active modes that become visible due to altered optical selection rules in field-gradient Raman conditions as described above.

FIG. 1B shows four field enhancement spectra created by four antenna pairs 11-14 (as in FIG. 1A), which yield a field enhancement sufficiently high to enable Raman spectroscopy on a single-molecule level, thereby creating detectable Raman signals as schematically shown in FIG. 1C.

2.3.2.2 Detection Mechanism Based on Optical Resonance Shifts

Changes in the local dielectric environment of a nano-photonic antenna cause shifts in the antenna's resonance. This can be the basis of a suitable detection mechanism for liquids (micro-fluidics, capillary-driven micro-fluidics, nano-fluidics, probe-based spectroscopy, etc.) or for molecules which permanently bind to the antenna due to a receptor layer functionalization. The measurements can be performed either by monitoring induced intensity and phase changes of the scattered light or through direct measurement of the resonance shifts. Stacked antennas further enable multiplexed operation at discrete wavelengths. Moreover, detecting optical resonance shifts requires less complicated instrumentation than detection of Raman scattered light.

In particular, the latter allows measurement of refractive index unit (RIU) changes with high sensitivity, e.g., $3.6 \, 10^{-4}$ RIU$\sqrt{Hz}$ of a 30 zeptoliter drop in the feed gap of a plasmonic bowtie antenna. This, in principle, allows oil droplets (n=1.4875) in water (n=1.33) to be detected/counted at a frequency exceeding 100 kHz. Monitoring of intensity or phase changes can even be expected to lead to better performance through shot-noise limited detection.

Figure 2B:
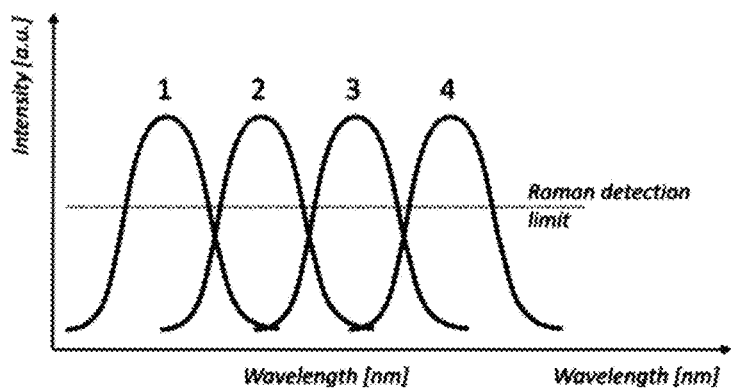
FIGS. 2B and 2C are graphs illustrating a corresponding detection scheme, which leverages resonance shifts induced by the presence of an analyte bound due to the receptor layers.
Figure 2C:
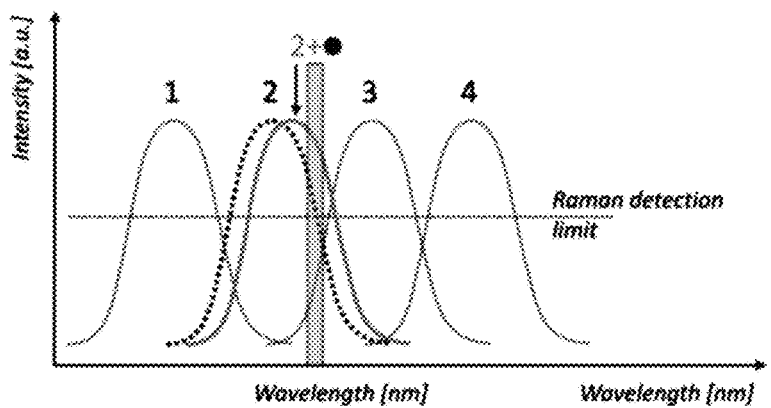

FIG. 2B shows four optical resonances of the four antenna pairs 11-14. As the resonance shifts depend only on the local dielectric environment (and not on the chemical bonds as in the former detection technique, sect. 2.3.2.1), the detector has to be made selective to certain analytes. Yet, complex spectrometric read-outs are no longer required and can be substituted for a photodiode in combination with suitably narrow band-pass filters or a narrow band light source, as symbolically depicted in FIG. 2C.

2.4 Preferred Sensing Techniques—Implementations

2.4.1 Excitation and Readout Implementations

Simple embodiments make use of standard Raman back-scattering geometries with external laser excitation and detection instruments (see FIG. 7) or as fully embedded waveguides and local excitation sources and detectors (FIGS. 8, 9). As said, the preferred fabrication methods are compatible with, e.g., selective area growth of III-V heterostructures, to create local lasers and photodetectors.

Notably, embodiments illustrated in FIGS. 8, 9 (with embedded waveguides and excitation as well as detection elements) do not require direct optical access. They can therefore be stacked in three dimensions to form 3D networks of nano-gaseous and nanofluidic channels with extremely high integration densities of the sensing elements.

2.4.2 Material Compositions

Antennas may consist of multiple materials and, in particular, selected materials 115 may be used to select analytes exposed to the antennas. Combining several materials further makes it possible to tailor resonances over broader spectral ranges, yield optical non-linearities and reduce losses. For instance, particular material combinations in distinct antenna portions can turn dark anti-bonding modes into far-field excitable sub-radiant modes, with reduced damping (and hence higher quality factors).

Moreover, antenna materials can be fully encapsulated to protect them against chemical degradation (e.g., oxidation) or physical damage (e.g., atom diffusion, thermal damage). The additional materials can also act as spacer layers between the analyte and the antennas, e.g., to avoid quenching in surface enhanced florescence measurements.

2.4.3 Electrical Contacts for Gating, Capacitance Measurements and Local Cooling and Heating It is further possible to electrically contact the antennas, for example in a crossbar structure without prohibitively disturbing the optical modes. A potential between the antennas can be used to either measure electrical capacitance changes or to induce ionizations of molecules for subsequent molecular sorting or to initiate chemical reactions due to the fields present (~1-10 V/nm).

Furthermore, electrically-driven Joule heating allow the antennas (or the contents, i.e., the analytes) to be heated. If the entire device is cooled by external means, e.g., a Peltier element, the antennas can also be controlled in temperature using the above mentioned effects. This may prove to be highly advantageous to bind analytes without receptor layers, enhance the binding of analytes in the receptor layer, clean the antennas, induce release of bound analytes and to locally trigger and control chemical reactions, especially where optical sensing elements are integrated in the devices (FIGS. 8-9). Additionally, the nano-antennas can, on their own, act as optically excitable local heat sources, with spectrally tunable absorption characteristics. Through channel-embedded heat-dissipating metal structures, possibly in conjunction with heat-transfer from adjacent channels with a coolant, the contents of the channel can also be cooled.

Figure 10:
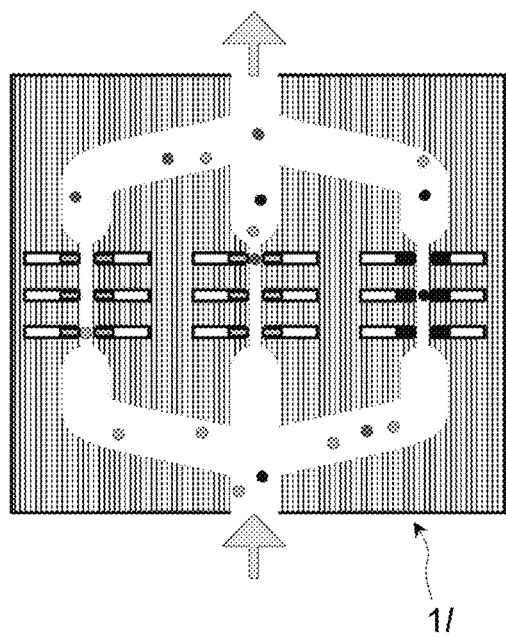
FIGS. 10-12 illustrate top views of more sophisticated optical sensing devices, comprising multiple channels of field-enhanced volumes, according to further embodiments. Such devices are particularly suited for: gas sensing (FIG. 10), nano-chemistry (FIG. 11), and nano-fluidics (FIG. 12)
Figure 11:
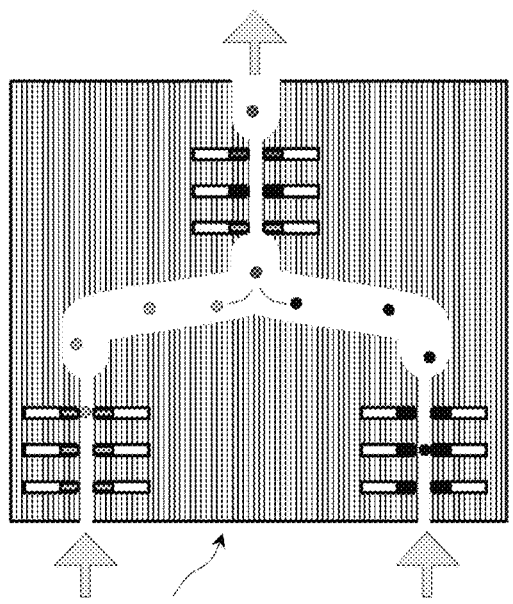
Figure 12:
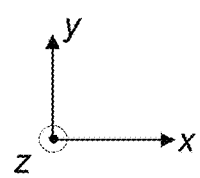
Figure 12:
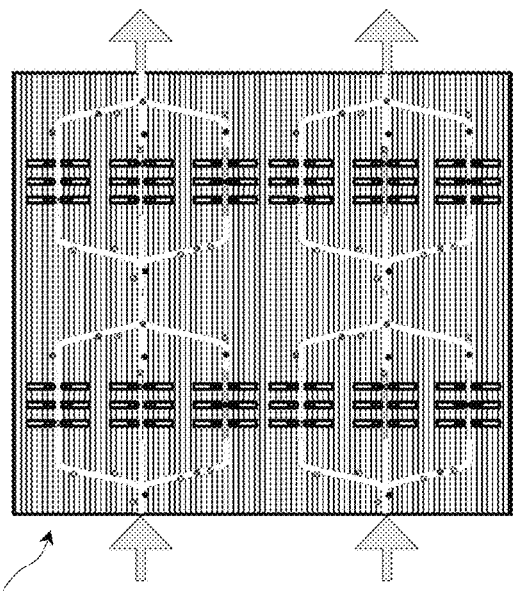

2.4.4 Multi-Dimensional Sensing Through Exploitation of Wavelength and Polarization Here, we also note that both wavelength and polarization can be employed to address specific hot-spots in sub-diffraction volumes, leading to high integration densities of sensor elements as well as multiplexing abilities (FIGS. 10-12). In particular, such configurations allow for simultaneous readout of educt and product responses in nano-chemical reactors. The channels can be oriented in complex networks to form mixers and separators, with the antennas acting as local sub-diffraction signal transducers.

Antennas with chosen symmetries can further be used to generate chiral fields or create far-field excitable sub-radiant modes with reduced damping and correspondingly higher field intensities (not shown). Namely, multi-resonance antennas can be stacked among different nano-channels and simultaneously read-out using their respective resonant wavelength. Moreover, polarization can be employed to specifically address an antenna in a sub-diffraction volume. Also, specific antenna geometries may generate chiral fields (circularly polarized light) and sub-radiant modes (azimuthally and radially polarized light) with even narrower quality factors.

2.4.5 Control Over Emission Characteristics and Increased Light Matter Confinement The preferred fabrication processes allows integration of elements underneath, around and above the antennas. For example, a reflector may be placed underneath the antenna, which helps to direct all of the emitted light towards the upper half-plane, thereby substantially enhancing collection efficiency in a far field detection configuration, e.g., as in FIGS. 7A-7B.

If necessary, additional functional elements underneath, beneath or above the antennas may be patterned to direct the emitted light towards specific directions, again aiding detection (not shown). It is further possible to grow multi-stack layers both below and above the antennas to create cavities and further enhance light-antenna interaction.

For instance, a reflector can also be an integral part of the antenna design, as in the case of patch antennas and monopole antennas. A small gap between antenna and reflector plane can be further exploited for enhancing the local fields and maximizing the interaction strength with analytes.

2.5 Examples of Applications

Given deterministic analytes delivery and strong field-enhancements as enabled in embodiments, a large range of applications can be contemplated. For example:

General sensing of different compounds in ultra-low volumes and with few-to-single molecule sensitivity (FIG. 10);
Multiplexed sensing (FIGS. 10-11);
Environmental monitoring of ppm concentrations;
Analysis of exhaled breath (for detecting volatile organic compounds, metabolites, etc.).
Nano-chemistry with educt and product analysis (FIG. 11);
Photo-catalysis;
Capillary-driven microfluidics (FIG. 12);
Capillary-driven and diffusion-based nano-fluidics;
Bio-material- and geo-material-microfluidics (FIG. 12);
Probe-based diagnostics;
Etc.

2.6 Final Considerations

Some of the methods described herein can be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip can then be integrated with other chips, discrete circuit elements, and/or other signal processing devices as part of either (a) an intermediate product, such as a motherboard, or (b) an end product. The end product can be any product that includes integrated circuit chips, ranging from low-end applications to advanced computerized detection products.

While the present invention has been described with reference to a limited number of embodiments, variants and the accompanying drawings, it will be understood by those skilled in the art that various changes may be made and equivalents may be substituted without departing from the scope of the present invention. In particular, a feature (device-like or method-like) recited in a given embodiment, variant or shown in a drawing may be combined with or replace another feature in another embodiment, variant or drawing, without departing from the scope of the present invention. Various combinations of the features described in respect of any of the above embodiments or variants may accordingly be contemplated, that remain within the scope of the appended claims. In addition, many minor modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims. In addition, many other variants than explicitly touched above can be contemplated. For example, other materials than those explicitly mentioned may be contemplated, as the skilled person will appreciate.

What is claimed is:

1. An optical sensing device comprising:
a substrate;
a first dielectric layer extending on the substrate;
a plurality of pairs of opposite antennas patterned on the first dielectric layer, wherein opposite antennas are, in each of the pairs, separated by a gap g, which, on average, is between 1 nm and 50 nm, as measured in a direction x parallel to a main plane of the substrate, and wherein the pairs of antennas have different geometries; and
a second dielectric layer that covers all of the antennas, so as to define an electro-magnetic field enhancement volume between the opposite antennas of each of the pairs, thanks to the gap g in between, in which volume electro-magnetic radiation can be concentrated for optically sensing an analyte via opposite antennas of each of the pairs, in operation.

2. The optical sensing device according to claim 1, wherein
the pairs of antennas have different lengths, the lengths measured between outermost ends of opposite antennas of each of the pairs along that same direction x.

3. The optical sensing device according to claim 1, wherein
the gaps separating the antennas of each of the pairs are essentially constant, subject to ±0.1 nm.

4. The optical sensing device according to claim 1, wherein
electro-magnetic field enhancement volumes defined between the antennas of each of the pairs are, each, between 1 $nm^3$ and $10^5$ $nm^3$.

5. The optical sensing device according to claim 1, wherein
opposite antennas within each of one of more of the pairs have different lengths, as measured along said direction x, or distinct geometries.

6. The optical sensing device according to claim 1, wherein
antennas of one of more of the pairs have a form factor, such that their largest dimension is parallel to said direction x.

7. The optical sensing device according to claim 1, further comprising
chemical receptor layers oppositely arranged on opposite, inner faces of opposite antennas of one of more of the plurality of pairs.

8. The optical sensing device according to claim 1, wherein
the device comprises a channel, along which opposite antennas of each of the pairs are arranged, in vis-à-vis, the channel configured so as to enable fluid communication between electro-magnetic field enhancement volumes defined between opposite antennas of each of the pairs.

9. The optical sensing device according to claim 8, wherein
opposite antennas of each of the pairs are patterned along a section of the channel that extends parallel to a direction y, which is parallel to the main plane of the substrate and perpendicular to said direction x, and wherein a minimal separation between contiguous pairs of antennas, as measured along said direction y, is of at least 1 nm.

10. The optical sensing device according to claim 8, wherein
one or each of the antennas of one or more of the pairs is at least partly embedded, laterally, in a dielectric structure, the latter shaped so as to define lateral walls of the channel, said walls extending perpendicular to the main plane of the substrate.

11. The optical sensing device according to claim 10, wherein
the substrate comprises a recess, over which the first dielectric layer extends, such that a recessed portion of the first dielectric layer is arranged on the recess, whereas a peripheral portion of the first dielectric layer extends over a peripheral region of the substrate, around the recess, whereby said recessed portion is recessed from said peripheral portion of the first dielectric layer, in a direction z perpendicular to the main plane of the substrate, and wherein:
said one or each of the antenna is patterned on the recessed portion of the first dielectric layer; and
the peripheral portion is further patterned so as to form the dielectric structure, in which said one or each of the antennas is at least partly embedded, laterally.

12. The optical sensing device according to claim 10, wherein
said one or each of the antennas is only partly embedded, laterally, in said dielectric structure, whereby a void is defined between said each one or each of the antennas and a portion of said dielectric structure.

13. The optical sensing device according to claim 12, wherein
said void is defined at an outermost end of said one or each antenna, with respect to the gap g separating said one or each antenna from an opposite one of the antennas.

14. The optical sensing device according to claim 10, wherein
the device further comprises waveguides at least partly embedded, laterally, in dielectric structures, in which antennas of the pairs are also at least partly embedded, laterally.

15. The optical sensing device according to claim 14, wherein
said waveguides are plasmonic, dielectric or photonic waveguides, and
the device further comprises, integrated therein, one or more of an electro-optical light source and an electro-optical light detector, coupled to a respective one of said waveguides.

16. The optical sensing device according to claim 15, wherein
one or each of said electro-optical light source and said electro-optical light detector is monolithically integrated in the optical sensing device.

17. An optical sensing system comprising:
an optical sensing device comprising:
- a substrate;
- a first dielectric layer extending on the substrate;
- a plurality of pairs of opposite antennas patterned on the first dielectric layer, wherein opposite antennas are, in each of the pairs, separated by a gap g, which, on average, is between 1 nm and 50 nm, as measured in a direction x parallel to a main plane of the substrate, and wherein the pairs of antennas have different geometries; and
- a second dielectric layer that covers all of the antennas, so as to define an electro-magnetic field enhancement volume between the opposite antennas of each of the pairs, thanks to the gap g in between, in which volume electro-magnetic radiation can be concentrated for optically sensing an analyte via opposite antennas of each of the pairs, in operation, and an electro-optical light source; and
an electro-optical light detector,
wherein
said electro-optical light source and said electro-optical light detector are configured for optically exciting the pairs of antennas and optically detecting signals therefrom, in a transmission geometry or a reflection geometry.

18. A method for optically sensing an analyte, the method comprising:
providing an optical sensing device comprising: a substrate; a first dielectric layer extending on the substrate; a plurality of pairs of opposite antennas patterned on the first dielectric layer, wherein opposite antennas are, in each of the pairs, separated by a gap g, which, on average, is between 1 nm and 50 nm, as measured in a direction x parallel to a main plane of the substrate, and wherein the pairs of antennas have different geometries; and a second dielectric layer that covers all of the antennas, such that a plurality of electro-magnetic field enhancement volumes are defined, each between the opposite antennas of each of the pairs, thanks to the gap g in between, in which volumes electro-magnetic radiation can be concentrated for optically sensing an analyte via opposite antennas of each of the pairs, in operation,
letting an analyte reach said electro-magnetic field enhancement volumes, while optically exciting the pairs of antennas of this device, to concentrate electromagnetic radiation in said volumes, and
optically detecting, via the plurality of pairs of opposite antennas, optical signals as modulated and/or generated by the analyte in said volumes.

19. The method according to claim 18, wherein
detecting comprises combining spectrally different field enhancements as obtained thanks to the pairs of antennas.

20. The method according to claim 18, wherein:
the optical sensing device provided further comprises chemical receptor layers oppositely arranged on opposite, inner faces of opposite antennas of one of more of the plurality of pairs; and
detecting comprises detecting resonance shifts induced by the presence of analyte bound due to the receptor layers.

* * * * *